United States Patent
Coates et al.

(10) Patent No.: US 10,464,928 B2
(45) Date of Patent: Nov. 5, 2019

(54) AMINO PYRIMIDINE SSAO INHIBITORS

(71) Applicant: Eli Lilly and Company, Indianapolis, IN (US)

(72) Inventors: David Andrew Coates, Indianapolis, IN (US); Luo Heng Qin, Indianapolis, IN (US); Yi Wei, Indianapolis, IN (US); Jingye Zhou, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/356,882

(22) Filed: Mar. 18, 2019

(65) Prior Publication Data

US 2019/0276436 A1    Sep. 12, 2019

Related U.S. Application Data

(63) Continuation of application No. 16/011,855, filed on Jun. 19, 2018, now Pat. No. 10,287,270, which is a continuation of application No. PCT/CN2017/095999, filed on Aug. 4, 2017.

(30) Foreign Application Priority Data

Aug. 12, 2016    (WO) ................ PCT/CN2016/094833

(51) Int. Cl.
| | |
|---|---|
| C07D 403/04 | (2006.01) |
| C07D 401/04 | (2006.01) |
| A61P 1/16 | (2006.01) |
| A61K 31/715 | (2006.01) |
| A61K 31/395 | (2006.01) |

(52) U.S. Cl.
CPC .......... *C07D 403/04* (2013.01); *A61K 31/395* (2013.01); *A61K 31/715* (2013.01); *A61P 1/16* (2018.01); *C07D 401/04* (2013.01)

(58) Field of Classification Search
None
See application file for complete search history.

(56) References Cited

U.S. PATENT DOCUMENTS

| | | |
|---|---|---|
| 8,716,470 B2 | 5/2014 | Yoshihara et al. |
| 9,302,986 B2 | 4/2016 | Deodhar et al. |
| 10,278,970 B2 | 5/2019 | Mengyang et al. |
| 10,287,270 B2 | 5/2019 | Coates et al. |
| 2014/0315882 A1 | 10/2014 | Fleck et al. |
| 2014/0343083 A1 | 11/2014 | Heine et al. |
| 2018/0296560 A1 | 10/2018 | Fan et al. |
| 2018/0297987 A1 | 10/2018 | Coates et al. |

FOREIGN PATENT DOCUMENTS

| | | |
|---|---|---|
| CN | 103459369 A | 12/2013 |
| CN | 104520268 A | 4/2015 |
| JP | 2011136942 A | 7/2011 |
| WO | WO-2008/123469 A1 | 10/2008 |
| WO | WO-2009/012573 A1 | 1/2009 |
| WO | WO-2009/066152 A2 | 5/2009 |
| WO | WO-2014/078609 A1 | 5/2014 |
| WO | WO-2016/042332 A1 | 3/2016 |
| WO | WO-2018/027892 A1 | 2/2018 |
| WO | WO-2018/028517 A1 | 2/2018 |
| WO | WO-2018/148856 A1 | 8/2018 |
| WO | WO-2018/149226 A1 | 8/2018 |

OTHER PUBLICATIONS

Jarolimek, W. et al. (Dec. 31, 2015). "Phase 1 Results from PXS-4728A, a Selective SSAO/V AP-1 Inhibitor, for 1-18 the Treatment of Non-Alcoholic Steatohepatitis," *Journal of Hepatology* 62:s274-s275.
Wang, Y. et al. (Apr. 20, 2016, e-pub. Apr. 4, 2016). "Enantioselective CuH-Catalyzed Hydroallylation of Vinylarenes," *Journal of the American Chemical Society* 138(15):5024-5027.
International Preliminary Report on Patentability dated Feb. 21, 2019, for Patent Application No. PCT/CN2016/094833, filed Aug. 12, 2016, 7 pages.
International Preliminary Report on Patentability dated Feb. 21, 2019, for Patent Application No. PCT/CN2017/095999, filed Aug. 4, 2017, 6 pages.
International Search Report and Written Opinion dated Apr. 20, 2018, for Patent Application No. PCT/US2018/017152, 8 pages.
International Search Report and Written Opinion of the International Searching Authority, dated Mar. 29, 2018, for Patent Application No. PCT/CN2017/000157, 8 pages.
International Search Report and Written Opinion dated Nov. 13, 2017, for application No. PCT/CN2017/095999, 8 pages.
International Search Report and Written Opinion of the International Searching Authority, dated May 16, 2017, for PCT Patent Application No. PCT/CN2016/094833, 10 pages.
International Search Report and Written Opinion of the International Searching Authority, dated Nov. 22, 2018, for PCT Patent Application No. PCT/CN2017/117791, 8 pages.
U.S. Appl. No. 16/356,895, filed Mar. 18, 2019, for Mengyang Fan et al.

*Primary Examiner* — Kamal A Saeed
(74) *Attorney, Agent, or Firm* — Morrison and Foerster LLP

(57) ABSTRACT

The present invention provides compounds of the Formula (I), or a pharmaceutically acceptable salt thereof, where n and R1 are defined herein, methods of treating patients for liver disease, and processes for preparing the compounds.

16 Claims, No Drawings

AMINO PYRIMIDINE SSAO INHIBITORS

CROSS REFERENCE TO RELATED APPLICATIONS

This application is a continuation of U.S. patent application Ser. No. 16/011,855, filed Jun. 19, 2018, which is a continuation of International Application No. PCT/CN2017/095999, filed Aug. 4, 2017, which claims priority benefit of International Application No. PCT/CN2016/094833, filed Aug. 12, 2016, the disclosures of each of which are incorporated herein by reference.

This invention relates to amino pyrimidine compounds, pharmaceutically acceptable salts of the compounds, and therapeutic uses of the compound and salts.

Semicarbazide-sensitive amino oxidase/vascular adhesion protein-1 (SSAO)/VAP-1) is a member of the semicarbazide-sensitive amino oxidase family. SSAO/VAP-1 has been alternatively referred to as VAP-1 or SSAO. SSAO/VAP-1 is an enzyme that exists both as a membrane-bound and a soluble isoform; it is predominantly expressed from endothelial cell surface, vascular smooth muscle and adipose cells. SSAO/VAP-1 participates in many cellular processes including glucose disposition, inflammation responses, and leukocyte recruitment. High activity levels of this enzyme are associated with diabetes, atherosclerosis, strokes, chronic kidney disease, and Alzheimer's disease, among other disorders. Recently SSAO/VAP-1 has been implicated in the pathogenesis of liver diseases such as fatty liver disease. Weston, C. J. et al., J Neural. Transm. 2011, 118, 1055-1064. Fatty liver disease (FLD) encompasses a spectrum of disease states where fat accumulates in the liver in excessive amounts and is accompanied by inflammation. FLD can lead to non-alcoholic fatty liver disease (NAFLD), which is characterized by insulin resistance. Unchecked NAFLD progresses to a persistent inflammatory response or non-alcoholic steatohepatitis (NASH), progressive liver fibrosis, and eventually to cirrhosis. Currently there is a need to provide alternative treatment therapies for liver diseases such as NAFLD and/or NASH.

It is thought that a SSAO/VAP-1 inhibitor will reduce liver inflammation and fibrosis and thereby provide a treatment for liver diseases, in particular, a treatment for NAFLD and/or NASH. The present invention provides compounds that inhibit the SSAO/VAP-1 enzyme and which may address one or more of the needs.

The present invention provides compounds of Formula 1:

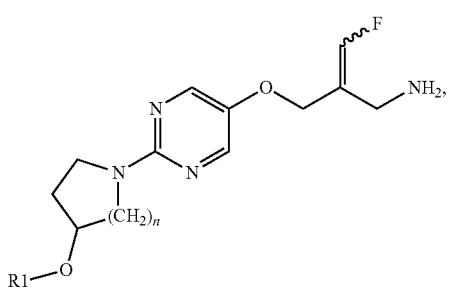

where n is 1 or 2; and R1 is H or —CH$_3$; or a pharmaceutically acceptable salt thereof. The bond to fluorine, which is illustrated as ⌇, indicates that the fluorine atom and the methoxypyrimidine group can be either Z (zusammen, together) or E (entgegen, opposite) relative to each other (Brecher, J., et al., "Graphical Representation of Stereochemical Configuration", Pure and Appl. Chem, 2006, 78(10) 1897, at 1959). The structure illustrated by Formula 1 includes compounds with the Z stereochemical configuration, the E stereochemical configuration, or a mixture of compounds in the Z or E stereochemical configurations. Preferred compounds of the invention have the E stereochemical configuration.

In one form, the present invention provides compounds of Formula 1 as a free base. In other form, the present invention provides compounds of Formula 1 as acid addition salts, such as a mono or di HCl addition salt(s) or a sulfonate salt, preferable a 4-methylbenzenesulfonate (a toslyate salt).

In one form, the present invention provides a compound of Formula 2:

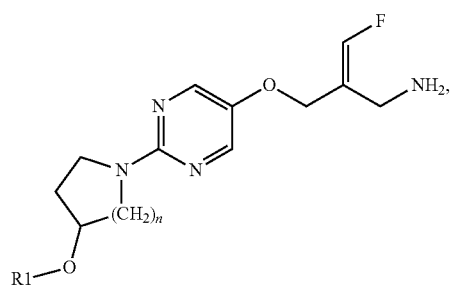

where n is 1 or 2; and R1 is H or —CH$_3$; or a pharmaceutically acceptable salt thereof.

In another form, the present the present invention provides a compound of Formula 3:

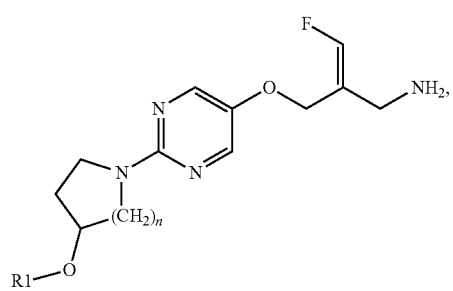

where n is 1 or 2; and R1 is H or —CH$_3$; or a pharmaceutically acceptable salt thereof.

In one embodiment, the present invention provides a compound according to one of Formulae 1, 2, and 3 where n is 1, or a pharmaceutically acceptable salt thereof. In another embodiment, the present invention provides a compound according to one of Formulae 1, 2, and 3 where n is 2, or a pharmaceutically acceptable salt thereof.

In another embodiment, the present invention provides a compound according to one of Formulae 1, 2, and 3 where R1 is H, or a pharmaceutically acceptable salt thereof. In yet another embodiment, the present invention provides a compound according to one of Formulae 1, 2, and 3 where R1 is —CH$_3$, or a pharmaceutically acceptable salt thereof.

In another form, the present invention provides a compound of Formula 4

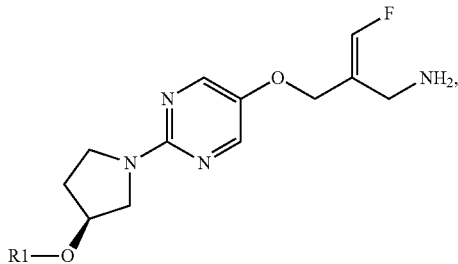

4 where R1 is H or —CH$_3$, or a pharmaceutically acceptable salt thereof.

In another form, the present invention provides a compound according to of Formula 5

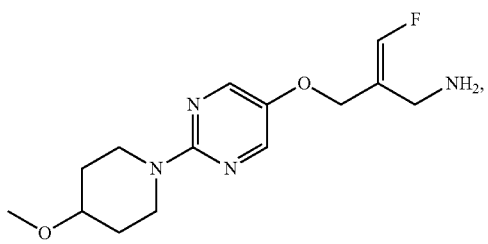

5 or a pharmaceutically acceptable salt thereof. In one embodiment, the compound of Formula 5 is provided as an acid addition salt. Preferably the acid addition salt is a mono or di HCl addition salt or a sulfonate salt, such as a methylsulfonic acid or 4-methylbenzenesulfonic acid addition salt to provide a mesylate salt or a 4-methylbenzenesulfonate (tosylate) salt.

In another form, the present invention provides a pharmaceutical composition comprising a compound according to any one of Formulae 1 to 5, or a pharmaceutically acceptable salt thereof, and a pharmaceutically acceptable carrier, diluent, or excipient. In one embodiment, the pharmaceutical composition comprises a compound according to Formula 5, or a pharmaceutically acceptable salt thereof. Preferably the pharmaceutically acceptable anion(s) for the salt is a mono or di chloride, mesylate or a 4-methylbenzenesulfonate (tosylate).

In another form, the present invention provides a method of treating a patient in need of treatment for liver disorder. The method comprises administering to the patient an effective amount of a pharmaceutical composition that comprises a compound according to any of Formulae 1 to 5, or a pharmaceutically acceptable salt thereof.

In another form, the present invention provides a method of treating a patient in need of treatment for a liver disorder. The method comprises administering to the patient an effective amount of a compound according to any one of Formulae 1 to 5, or a pharmaceutically acceptable salt thereof. Examples of liver disorders include liver inflammation, fibrosis, and steatohepatitis. In certain embodiments, the method comprises treating a patient in need of treatment for a liver disorder where the liver disorder is selected from: liver fibrosis, alcohol induced fibrosis, alcoholic steatosis, non-alcoholic fatty liver disease (NAFLD), and non-alcoholic steatohepatitis (NASH). In a particularly preferred embodiment, the method comprises treating a patient in need of treatment for non-alcoholic steatohepatitis (NASH).

In another form, the present invention provides a compound of Formula 6, which is a (2E)-3-Fluoro-2-({[2-(4-methoxypiperidin-1-yl)pyrimidin-5-yl]oxy}methyl)prop-2-en-1-amine 4-methylbenzenesulfonate (1:1) salt.

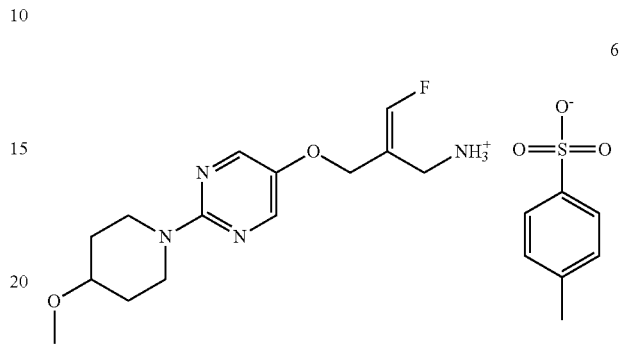

6

In one embodiment, the (2E)-3-Fluoro-2-({[2-(4-methoxypiperidin-1-yl)pyrimidin-5-yl]oxy}methyl)prop-2-en-1-amine 4-methylbenzenesulfonate (1:1) salt is provided in crystalline form characterized by an X-ray powder diffraction pattern obtained from a CuKα source (λ=1.54056 Å), which comprises peaks at: a) 18.6, 19.1, 21.0, 21.9, and 22.4+/−0.2° in 2 theta, or b) 17.6, 11.0, 16.8, 18.6, 19.1, 21.0, 21.9, 22.4 and 26.1+/−0.2° in 2 theta.

In another form, the present invention provides a compound according to any one of Formulae 1 to 6, or a pharmaceutically acceptable salt thereof, for use in therapy. In preferred embodiments, the therapy is for a liver disorder. Preferably, the therapy is for a liver disorder selected from: liver fibrosis, alcohol induced fibrosis, alcoholic steatosis, non-alcoholic fatty liver disease, and non-alcoholic steatohepatitis. In one embodiment, the therapy is for the treatment of liver fibrosis. In another embodiment, the therapy is for non-alcoholic fatty liver disease. In still yet another embodiment, the therapy is for non-alcoholic steatohepatitis.

In another form, the present invention provides a compound according to any one of Formulae 1 to 6, or a pharmaceutically acceptable salt thereof, for use in the treatment of a liver disorder. In one embodiment, the liver disorder is selected from: liver fibrosis, alcohol induced fibrosis, alcoholic steatosis, non-alcoholic fatty liver disease, and non-alcoholic steatohepatitis. In another embodiment, the liver disorder is non-alcoholic fatty liver disease or non-alcoholic steatohepatitis. In a particularly preferred embodiment, the liver disorder is non-alcoholic steatohepatitis (NASH).

In yet another embodiment, the present invention provides for the use of a compound according to any one of Formulae 1 to 6 in the manufacture of a medicament to treat a liver disorder. In preferred embodiments, the liver disorder is selected from: liver fibrosis, alcohol induced fibrosis, alcoholic steatosis, non-alcoholic fatty liver disease, and non-alcoholic steatohepatitis.

The term "pharmaceutically-acceptable salt" as used herein refers a salt of a compound of the invention considered to be acceptable for clinical and/or veterinary use. Examples of pharmaceutically acceptable salts and common methodology for preparing them can be found in "Handbook of Pharmaceutical Salts: Properties, Selection and Use" P.

Stahl, et al., 2nd Revised Edition, Wiley-VCH, 2011 and S. M. Berge, et al., "Pharmaceutical Salts", *Journal of Pharmaceutical Sciences*, 1977, 66(1), 1-19.

The pharmaceutical compositions for the present invention may be prepared using pharmaceutically acceptable additives. The term "pharmaceutically acceptable additive(s)" as used herein for the pharmaceutical compositions, refers to one or more carriers, diluents, and excipients that are compatible with the other additives of the compositions or formulations and not deleterious to the patient. Examples of pharmaceutical compositions and processes for their preparation can be found in "Remington: The Science and Practice of Pharmacy", Loyd, V., et al. Eds., 22$^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; polyethyl glycols.

As used herein, the term "effective amount" refers to an amount that is a dosage, which is effective in treating a disorder, such as a liver disease including liver inflammation, fibrosis, and steatohepatitis. The attending physician, as one skilled in the art, can readily determine an effective amount by the use of conventional techniques and by observing results obtained under analogous circumstances. In determining an effective amount or dose of a compound, a number of factors are considered, including, but not limited whether the compound or its salt, will be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

As used herein, the terms "treating", "to treat", or "treatment", includes slowing, reducing, or reversing the progression or severity of an existing symptom, disorder, condition, or disease, which can include treating liver disease, such as, liver inflammation, fibrosis, and steatohepatitis.

As used herein, the term "patient" refers to a mammal, fowl, or fish. Preferably, the patient is a human or companion mammal, such as, a dog or cat or other domesticated mammal, such as, a cow, pig, horse, sheep, rabbit, and goat.

A treating physician, veterinarian, or other medical person will be able to determine an effective amount of the compound for treatment of a patient in need. Preferred pharmaceutical compositions can be formulated as a tablet or capsule for oral administration, a solution for oral administration, or an injectable solution. The tablet, capsule, or solution can include a compound of the present invention in an amount effective for treating a patient in need of treatment.

The abbreviations used herein are defined according to Daub G. H., et al., "The Use of Acronyms in Organic Chemistry" *Aldrichimica Acta*, 1984, 17(1), 6-23. Other abbreviations are defined as follows: "ACN" refers to acetonitrile; "AUC" refers to area under the curve; "Boc" represents tert-butoxycarbonyl; "DCM" refers to dichloromethane; "DIPEA" refers to N,N-diisopropylethylamine; "DMF" refers to dimethylformamide; "DMSO" refers to dimethylsulfoxide; "EDTA" refers to ethylenediaminetetraacetic acid; "EGTA" refers to ethylene glycol tetraacetic acid; "ES/MS" refers to electrospray mass spectroscopy; "EtOAc" refers to ethyl acetate; "HEPES" refers to 4-(2-hydroxyethyl)-1-piperazineethanesulfonic acid; "HPLC" refers to high performance liquid chromatography; "hr or hrs" refers to hour or hours; "HRP" refers to horse radish peroxidase; "IC$_{50}$" refers to the concentration of an agent which produces 50% of the maximal inhibitory response possible for that agent (relative IC$_{50}$), or the concentration of an agent which produces 50% inhibition of the target activity compared to placebo control (absolute IC$_{50}$); "MAOa and MAOb" refers to monoamine oxidas a and b isoform, respectively; "MeOH" refers to methyl alcohol or methanol; "min" refers to minutes; "MS" refers to mass spectroscopy; "PE" refers to petroleum ether; "R$_t$" refers to retention time; "SSAO" refers to semicarbazide-sensitive amine oxidase; and "hSSAO" refers to human SSAO.

The compounds of the present invention, or salts thereof, may be prepared by a variety of procedures, some of which are illustrated in the Preparations, and the Examples below. The product(s) of each step in the procedures below can be recovered by conventional methods including extraction, evaporation, precipitation, chromatography, filtration, trituration, and crystallization. Unless noted to the contrary, the reagents and starting materials are readily available.

In the preparations described herein the hydroxyl and amino functionalities can be protected to facilitate the synthesis of the compounds described herein. Examples of protecting functionalities can be found in "Greene's Protective Groups in Organic Synthesis," Wuts, P. G. M., et al., Eds. 5th Ed., John Wiley and Sons, 2014. Other functional groups that can be readily converted to the hydroxyl group or the amino group can be used. Such functional groups, preparations, and transformations of these groups can be found in "Comprehensive Organic Transformations: A Guide to Functional Group Preparations" by Larock. R. C., Wiley VCH, 1999 and in "March's Advanced Organic Chemistry: Reactions, Mechanisms and Structure," Smith, M. B., Ed., 7th Ed., Wiley-Interscience, 2013.

Chemical Synthesis Section

The following Preparations and Examples further illustrate the invention and represent typical synthesis of the compounds of the invention.

Preparation 1 tert-Butyl (3S)-3-methoxypyrrolidine-1-carboxylate

Add iodomethane (0.398 g, 2.80 mmol) to a mixture of tert-butyl (3S)-3-hydroxypyrrolidine-1-carboxylate (0.500 g, 2.67 mmol) and sodium hydride (60 mass % in mineral oil) (0.160 g, 4.01 mmol) in DMF (5 mL). Stir the resulting mixture at room temperature for 2 hours. Quench the reaction with saturated aqueous NH$_4$Cl aq. (30 mL) and extract with EtOAc (3×30 mL). Discard the aqueous layer. Combine the organic extracts and wash with brine, dry over Na$_2$SO$_4$, filter, and evaporate the filtrate to dryness to give the title compound (475 mg, 0.475 g, 88.4%). The crude material can be used in the next step without further purification. ES/MS (m/z): 224.2 (M+Na).

Preparation 2

(3 S)-3-Methoxypyrrolidine

Stir a solution of tert-butyl (3S)-3-methoxypyrrolidine-1-carboxylate (475 mg, 2.36 mmol) and trifluoroacetic acid (1 mL, 13.23 mmol) in DCM (3 mL) at room temperature for 1 hour. Concentrate the reaction mixture under vacuum to give the title compound (240 mg, 2.35 mmol, 99.5%), which can be used in the next step without further purification.

Preparation 3

1-(5-Benzyloxypyrimidin-2-yl)piperidin-4-ol

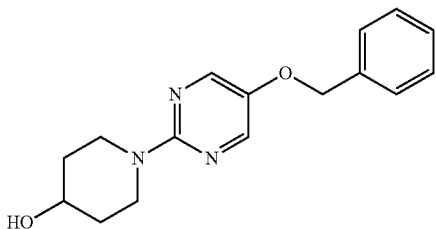 [SMILES: OC1CCN(c2ncc(OCc3ccccc3)cn2)CC1]

Stir a mixture of 5-benzyloxy-2-chloro-pyrimidine (2.30 g, 9.90 mmol), piperidin-4-ol (1.23 g, 11.9 mmol) and DIPEA (3.88 mL, 29.7 mmol) in DMF (30 mL, 388 mmol) at 100° C. under a N$_2$ atmosphere for 17 hrs. Dilute the mixture with water (200 mL) and extract with EtOAc (3×50 mL). Combine the organic extracts; wash with brine (3×50 mL), dry over Na$_2$SO$_4$, filter, and concentrate the filtrate. Subject the residue to silica gel flash column chromatography eluting with a mixture of 60% EtOAc and 40% PE to give the title compound (2.00 g, 6.31 mmol, 63.7%) as a white solid. $^1$H NMR (400 MHz, CDCl$_3$) δ 1.40-1.60 (m, 2H), 1.90-1.99 (m, 2H), 3.17-3.29 (m, 2H), 3.85-3.95 (m, 1H), 4.25-4.39 (m, 2H), 5.09 (s, 2H), 7.38-7.52 (m, 5H), 8.14 (s, 2H).

Preparation 4

2-(4-Hydroxy-1-piperidyl)pyrimidin-5-ol

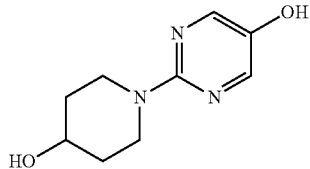 [SMILES: Oc1cnc(N2CCC(O)CC2)nc1]

Add palladium (10 mass % on carbon, 600 mg, 0.564 mmol) to 1-(5-benzyloxypyrimidin-2-yl)piperidin-4-ol (2.00 g, 6.31 mmol) in MeOH (40 mL, 989 mmol). Stir the resulting mixture at 15° C. under a hydrogen atmosphere (103 kPa) for 2 hrs. Filter the resulting mixture through diatomaceous earth. Concentrate the filtrate to give the title compound (0.70 g, 3.59 mmol, 56.8%) as a yellow solid. $^1$H NMR (400 MHz, CDCl$_3$) δ 1.23-1.38 (m, 2H), 1.60-1.77 (m, 2H), 2.65-2.90 (m, 2H), 3.00-3.25 (m, 2H), 3.50-3.70 (m, 2H), 4.05-4.16 (m, 1H), 7.90 (s, 2H).

Preparation 5 tert-Butyl N-[(E)-2-[(2-chloropyrimidin-5-yl)oxymethyl]-3-fluoro-allyl]carbamate

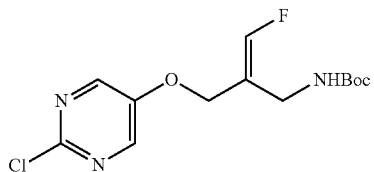 [SMILES: CC(C)(C)OC(=O)NC/C(=C\F)COc1cnc(Cl)nc1]

Add K$_2$CO$_3$ (5.71 g, 41.3 mmol) to a solution of 2-chloropyrimidin-5-ol (5.01 g, 38.3 mmol) and tert-butyl N-[(E)-2-(bromomethyl)-3-fluoro-allyl]carbamate (3.67 g, 13.7 mmol) in DMF (25 mL). Stir the resulting solution at room temperature for 12 hours. Quench the reaction by adding water (80 mL) and EtOAc (100 mL). Separate the organic and aqueous phases. Extract the aqueous phase with EtOAc (3×100 mL). Combine all the organic extracts. Dry the combined organic extracts over Na$_2$SO$_4$, filter, and concentrate the filtrate under vacuum to provide a residue. Subject the residue to silicia gel flash chromatography eluting with a mixture of 30% EtOAc in hexanes to give the title compound as a white solid (4.15 g, 13.1 mmol, 96% yield). ES/MS (m/z): 340 (M+Na).

Preparation 6 tert-Butyl N—[(Z)-3-fluoro-2-[[2-(4-hydroxy-1-piperidyl)pyrimidin-5-yl]oxymethyl]allyl]carbamate

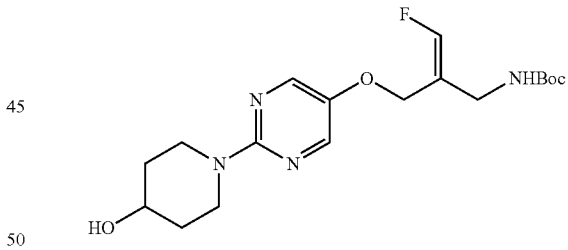

Stir a mixture of 2-(4-hydroxy-1-piperidyl)pyrimidin-5-ol (400 mg, 2.05 mmol), tert-butyl N—[(Z)-2-(bromomethyl)-3-fluoro-allyl]carbamate (1.10 g, 4.02 mmol) and K$_2$CO$_3$ (0.858 g, 6.15 mmol) in DMF (10 mL) at 60° C. for 3 hrs. Dilute the resulting mixture with EtOAc (50 mL). Sequentially wash the mixture with water (100 mL) then brine (2×50 mL). Dry the organic phase over Na$_2$SO$_4$, filter, and concentrate the filtrate to provide a residue. Subject the residue to silica gel flash column chromatography eluting with a gradient of 65-75% EtOAc in PE to give the title compound (558 mg, 1.46 mmol, 71.2%) as a yellow gum. $^1$H NMR (400 M Hz, CDCl$_3$) δ 1.25 (s, 9H), 1.40-1.65 (m, 4H), 1.89-1.98 (m, 2H), 3.23-3.30 (m, 2H), 3.91 (s, 1H), 3.89-3.97 (m, 1H), 4.36-4.40 (m, 2H), 4.64 (s, 2H), 4.76 (br, 1H), 6.62 (d, J=84.0 Hz, 1H) 8.10 (s, 2H).

Preparation 7 tert-Butyl N-[(E)-3-F-2-[[2-(4-hydroxy-1-piperidyl)pyrimidin-5-yl]oxymethyl]allyl]carbamate

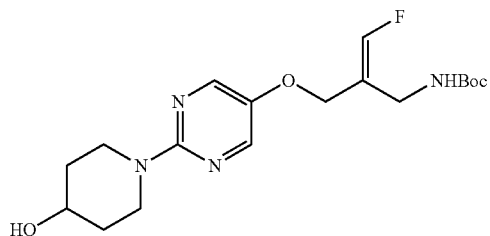 [SMILES: CC(C)(C)OC(=O)NC/C(=C\F)COc1cnc(N2CCC(O)CC2)nc1]

Combine tert-butyl N-[(E)-2-[(2-chloropyrimidin-5-yl)oxymethyl]-3-fluoro-allyl]carbamate (21.3 g, 67.0 mmol), piperidin-4-ol (25.0 g, 235 mmol), and DIPEA (41 mL, 235 mmol) in 1,4-dioxane (200 mL). Heat the resulting mixture to 105° C. under a $N_2$ atmosphere for 7 hours. Concentrate the mixture and partition it between water (100 mL) and EtOAc (150 mL), then separate the phases. Extract the aqueous phase with EtOAc (100 mL). Combine all the organic phases. Wash with brine (100 mL), dry over $Na_2SO_4$, filter, and concentrate the filtrate to provide a residue. Dissolve the residue in EtOAc (21 mL), and then drop-wise add heptane (126 mL). Stir the resulting mixture at room temperature for 20 hours. Filter the mixture to collect the solid, rinse the solid with EtOAc/heptane (5:1, 21 mL). Dry the solid under vacuum to give the title compound (23.5 g, 61.5 mmol, 91.7%). ES/MS (m/z): 383 (M+H).

Preparation 8 tert-Butyl N-[(E)-3-fluoro-2-[[2-(4-methoxy-1-piperidyl)pyrimidin-5-yl]oxymethyl]allyl]carbamate

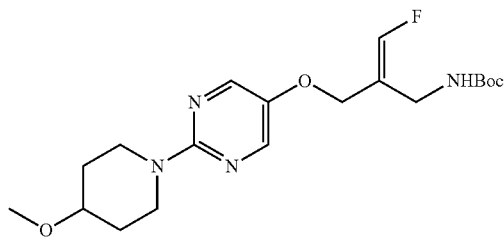 [SMILES: COC1CCN(c2ncc(OC/C(=C/F)CNC(=O)OC(C)(C)C)cn2)CC1]

Divide tert-butyl N-[(E)-2-[(2-chloropyrimidin-5-yl)oxymethyl]-3-fluoro-allyl]carbamate (4.10 g, 12.9 mmol) into 2 equal parts (2.05 g+2.05 g) and place each part into a separate microwave vial (20 mL). Into each vial, add 4-methoxypiperidine (4.31 g, 37.3 mmol), 1,4-dioxane (30 mL, 15 mL) and DIPEA (6 mL, 34.4 mmol, 3 mL). Flush the vials with $N_2$ gas, seal, and heat to 120° C. for 12 hours by microwave. Combine the two reaction mixtures and concentrate under vacuum to provide a residue. Subject the residue silica gel flash chromatography eluting with a mixture of 30% EtOAc in hexanes to give the title compound as a yellow oil (4.24 g, 10.2 mmol, 79%). ES/MS (m/z): 397 (M+H).

Preparation 9 tert-Butyl N-[(E)-3-fluoro-2-[[2-[(3S)-3-methoxypyrrolidin-1-yl]pyrimidin-5-yl]oxymethyl]allyl]carbamate

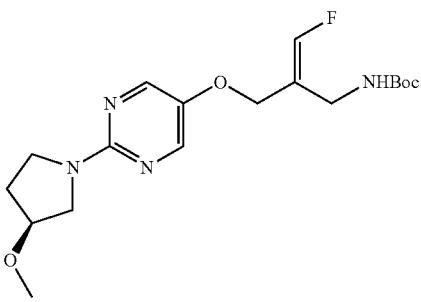 [SMILES: CO[C@H]1CCN(c2ncc(OC/C(=C/F)CNC(=O)OC(C)(C)C)cn2)C1]

Add tert-butyl N-[(E)-2-[(2-chloropyrimidin-5-yl)oxymethyl]-3-fluoro-allyl]carbamate (400 mg, 1.26 mmol) to a mixture of (3S)-3-methoxypyrrolidine (240 mg, 2.37 mmol) and $K_2CO_3$ (0.696 g, 5.04 mmol) in 1,4-dioxane (5 mL). Stir the resulting mixture at 120° C. under microwave conditions for 12 hours. Concentrate the mixture under vacuum to provide the title compound as a crude material, which can be used in the next step without further purification (481 mg, 1.26 mmol, 99.9%). ES/MS (m/z): 383.2 (M+H).

Preparation 10 tert-Butyl N-[(E)-3-fluoro-2-[[2-[(3S)-3-hydroxypyrrolidin-1-yl]pyrimidin-5-yl]oxymethyl]allyl]carbamate

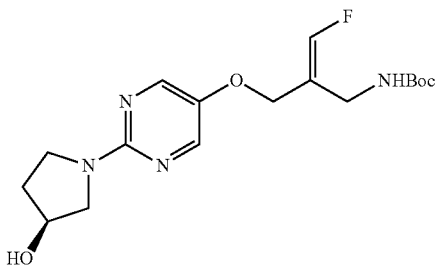 [SMILES: CC(C)(C)OC(=O)NC/C(=C\F)COc1cnc(N2CC[C@H](O)C2)nc1]

Dissolve tert-butyl N-[(E)-2-[(2-chloropyrimidin-5-yl)oxymethyl]-3-fluoro-allyl]carbamate (594.3 mg, 1.87 mmol) and (3S)-pyrrolidin-3-ol (488.9 mg, 5.61 mmol) in 1,4-dioxane (15 mL) and DIPEA (3 mL, 17.2 mmol). Flush the solution with $N_2$ gas, seal the vessel, and heat the mixture to 120° C. for 12 hours by microwave. Concentrate the resulting mixture under vacuum to provide a residue. Subject the residue to silica gel flash chromatography eluting with a gradient of 80-90% EtOAc in hexanes to give the title compound as a yellow foam (608.8 mg, 1.57 mmol, 84%). ES/MS (m/z): 369 (M+H).

EXAMPLE 1

1-[5-[(Z)-2-(Aminomethyl)-3-fluoro-allyloxy]pyrimidin-2-yl]piperidin-4-ol hydrochloride

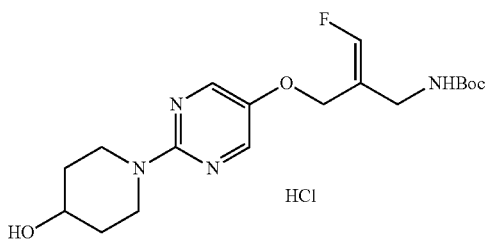 [SMILES: CC(C)(C)OC(=O)NC/C(=C/F)COc1cnc(N2CCC(O)CC2)nc1 ; Cl]

Add tert-butyl N—[(Z)-3-fluoro-2-[[2-(4-hydroxy-1-piperidyl)pyrimidin-5-yl]oxymethyl]allyl]carbamate (558 mg, 1.46 mmol) to HCl (4 mol/L) and MeOH (10 mL). Stir the resulting mixture for 1.5 hrs at 10° C. Concentrate the mixture under reduced pressure to provide a residue. Subject the residue to prep-HPLC column: (Phenomenex Synergi C18 150 30 mm, 4 µm) eluting with a gradient of 10 to 15% 0.05% aqueous HCl in ACN; flow rate: 25 mL/min, $R_t$: 5.95 min to give the title compound with a Z:E ratio of greater than 20:1 (456 mg, 1.43 mmol, 98.0%) as a yellow solid. ES/MS (m/z): 283.1 (M+H), $^1$H NMR (400 MHz, $d_4$-MeOD) δ 1.56-1.78 (m, 2H), 1.92-2.13 (m, 2H), 3.61-3.72 (m, 2H), 3.75 (s, 2H), 3.95-4.06 (m, 1H), 4.11-4.25 (m, 2H), 4.89-4.93 (m, 2H), 7.19 (d, J=80.4 Hz, 1H), 8.47 (s, 2H).

EXAMPLE 2

1-[5-[(E)-2-(Aminomethyl)-3-fluoro-allyloxy]pyrimidin-2-yl]piperidin-4-ol dihydrochloride

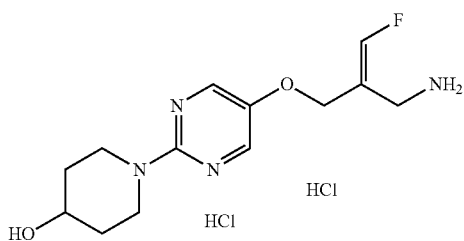 [SMILES: NC/C(=C\F)COc1cnc(N2CCC(O)CC2)nc1 ; Cl ; Cl]

Combine tert-butyl N-[(E)-3-fluoro-2-[[2-(4-hydroxy-1-piperidyl)pyrimidin-5-yl]oxymethyl]allyl]carbamate (31 g, 81.07 mmol), MeOH (20 mL, 494 mmol), and HCl in MeOH (120 mL, 4 mol/L, 486.4 mmol). Stir the resulting mixture for 30 hours under a $N_2$ atmosphere at room temperature. Add EtOAc (250 mL) drop-wise and stir the mixture for 30 minutes. Filter the mixture to collect the solid, rinse the solid with EtOAc (20 mL), and the dry the solid under vacuum to give the title compound with an E:Z ratio of greater than 20:1 (26.4 g, 72.8 mmol, 89.8%). ES/MS (m/z): 283 (M+H), $^1$H NMR (500 MHz, $d_6$-DMSO) δ 1.28-1.36 (m, 2H), 1.73-1.76 (m, 2H), 3.18-3.25 (m, 2H), 3.55-3.60 (m, 2H), 3.68-3.75 (m, 1H), 4.18 (dt, J=13.5, 4.5 Hz, 2H), 4.65 (d, J=3.0 Hz, 2H), 6.55-7.10 (br, 2H), 7.27 (d, J=82.0 Hz, 1H), 8.27 (s, 2H), 8.32-8.45 (br, 3H), $^{19}$F NMR (500 MHz, $d_6$-DMSO) δ 122.2 (s).

EXAMPLE 3

(E)-3-Fluoro-2-[[2-(4-methoxy-1-piperidyl)pyrimidin-5-yl]oxymethyl]prop-2-en-1-amine, Dihydrochloride

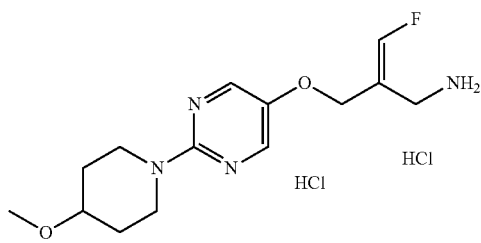 [SMILES: COC1CCN(c2ncc(OC/C(=C/F)CN)cn2)CC1 ; Cl ; Cl]

Dissolve tert-butyl N-[(E)-3-fluoro-2-[[2-(4-methoxy-1-piperidyl)pyrimidin-5-yl]oxymethyl]allyl]carbamate (4.2374 g, 10.69 mmol) in HCl in MeOH (100 mL, 50 mmol, 0.5 mol/L). Heat the resulting clear solution to 60° C. for 4 hours. Concentrate the mixture under vacuum to provide a residue (3.95 g). Suspend the residue in MeOH (7 mL) and reflux the mixture to provide a clear solution. Cool the solution to room temperature to give needle crystals, and then cool the mixture to −20° C. Filter the mixture to collect the solid, wash the solid with cool MeOH to give the title compound as light yellow crystals (2.73 g, 7.01 mmol, 66%). The resulting yellow crystals can be further purified via recrystallization with the same procedure described above to give the title compound as colorless, crystalline material with an E:Z ratio of greater than 20:1 ES/MS (m/z): 297 (M+H), $^1$H NMR (500 MHz, $d_6$-DMSO) δ 1.33-1.40 (m, 2H), 1.84-1.89 (m, 2H), 3.26 (dt, J=13.5, 9.5 Hz, 2H), 3.27 (s, 3H), 3.40-3.45 (m, 1H), 3.56-3.62 (m, 2H), 4.11 (dt, J=13.5, 5.0 Hz, 2H), 4.62 (d, J=3.0 Hz, 2H), 5.26-5.94 (br, 1H), 7.27 (d, J=82.0 Hz, 1H), 8.26 (s, 2H), 8.21-8.31 (br, 3H), $^{19}$F NMR (500 MHz, $d_6$-DMSO) δ 122.1 (s).

EXAMPLE 4

(E)-3-fluoro-2-[[2-(4-methoxy-1-piperidyl)pyrimidin-5-yl]oxymethyl]prop-2-en-1-amine

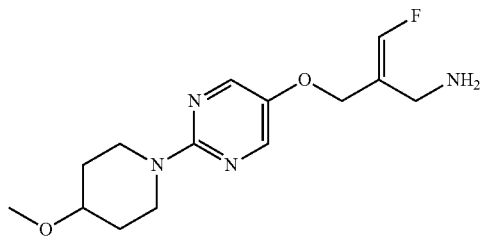 [SMILES: COC1CCN(c2ncc(OC/C(=C/F)CN)cn2)CC1]

Dissolve N-[(E)-3-Fluoro-2-[[2-(4-methoxy-1-piperidyl)pyrimidin-5-yl]oxymethyl]allyl] carbamate (167.0 mg, 0.42 mmol) in 0.95M HCl solution in 18 mL EtOAc/MeOH (10:1 v/v). Stir the mixture overnight. Concentrate the resulting suspension under vacuum and dissolve the residue in water. Subject the residue to pre-HPLC; LC column: XBridge® C18 30×150 mm 5 µm; eluting with a gradient of 14 to 24% 10 mM $NH_4HCO_3$ aqueous solution in ACN from 0-11 minutes; column temperature: room temperature; flow rate:

35 mL/min, $R_t$=7.8 minutes stopping after 17 min. monitor by UV. Collect and concentrate the appropriate fractions to provide a residue as an oil. The residue is dissolved in water and lyophilized to give the title compound as a white solid with an E:Z ratio greater than 20:1 (97 mg, 0.31 mmol, 74%, 95% purity). ES/MS (m/z): 297 (M+H), $^1$H NMR (500 MHz, $d_6$-DMSO) δ 1.33-1.41 (m, 2H), 1.52-1.69 (br, 1H), 1.83-1.89 (m, 2H), 3.23-3.29 (m, 4H), 3.27 (s, 3H), 3.30-3.35 (br, 1H), 3.38-3.44 (m, 1H), 4.11 (dt, J=13.5, 4.5 Hz, 2H), 4.55 (d, J=4.5 Hz, 2H), 6.93 (d, J=85.0 Hz, 1H), 8.22 (s, 2H), $^{19}$F NMR (500 MHz, $d_6$-DMSO) δ 131.8 (s).

EXAMPLE 4a (2E)-3-Fluoro-2-({[2-(4-methoxypiperidin-1-yl)pyrimidin-5-yl]oxy}methyl)prop-2-en-1-amine 4-methylbenzenesulfonate (1:1)

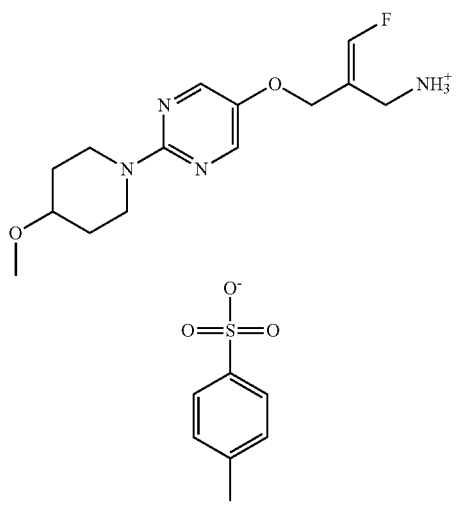

Dissolve (E)-3-fluoro-2-[[2-(4-methoxy-1-piperidyl)pyrimidin-5-yl]oxymethyl]prop-2-en-1-amine (2.316 g, 7.81 mmol) in methyl acetate (3 mL) and stir at 1000 rpm at room temperature to give a light yellow solution. Add 4-toluenesulfonic acid monohydrate (1.62 g, 8.43 mmol) in a solution of methyl acetate (4 mL). The mixture becomes cloudy and a thick yellow slurry quickly forms. Filter the solid by vacuum filtration through filter paper. Rinse the filter cake with methyl acetate (4 mL) to give a white filter cake. Dry the solid under a vacuum air stream for 10 minutes and then in a vacuum oven at room temperature overnight to give the title compound (3.00 g, 81.8%).

X-Ray Powder Diffraction of Example 4a

The X-ray powder diffraction (XRD) pattern of crystalline (2E)-3-fluoro-2-({[2-(4-methoxypiperidin-1-yl)pyrimidin-5-yl]oxy}methyl)prop-2-en-1-amine 4-methylbenzenesulfonate is obtained on a Bruker D4 Endeavor X-ray powder diffractometer, equipped with a CuKα source (λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of± 0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. Collect the crystal form diffraction patterns at ambient temperature and relative humidity and adjust based on NIST 675 standard peaks at 8.853 and 26.774 degrees 2-theta.

A prepared sample of (2E)-3-fluoro-2-({[2-(4-methoxypiperidin-1-yl)pyrimidin-5-yl]oxy}methyl)prop-2-en-1-amine 4-methylbenzenesulfonate is characterized by an XRD pattern using CuKα radiation as having diffraction peaks (2-theta values) as described in Table 1 below, and in particular having peaks at 18.6 in combination with one or more of the peaks selected from 22.4, 19.1, and 21.0; with a tolerance for the diffraction angles of +/−0.2° in 2 theta alternatively the salt can be characterized an XRD pattern having one or more peaks at 18.6, 19.1, 21.0, 21.9, and 22.4+/−0.2° in 2 theta, or 17.6, 11.0, 16.8, 18.6, 19.1, 21.0, 21.9, 22.4 and 26.1+/−0.2° in 2 theta.

TABLE 1

X-ray powder diffraction peaks of (2E)-3-fluoro-2-({[2-(4-methoxypiperidin-1-yl)pyrimidin-5-yl]oxy}methyl)prop-2-en-1-amine 4-methylbenzenesulfonate

| Peak | Angle (°2-Theta) +/− 0.2° | Relative Intensity (% of most intense peak) |
| --- | --- | --- |
| 1 | 7.4 | 17.6% |
| 2 | 11.0 | 23.4% |
| 3 | 12.7 | 5.2% |
| 4 | 16.8 | 10.1% |
| 5 | 18.6 | 100.0% |
| 6 | 19.1 | 42.2% |
| 7 | 21.0 | 41.9% |
| 8 | 21.9 | 31.6% |
| 9 | 22.4 | 77.5% |
| 10 | 26.2 | 18.6% |

EXAMPLE 5

(E)-3-Fluoro-2-[[2-[(3S)-3-methoxypyrrolidin-1-yl]pyrimidin-5-yl]oxymethyl]prop-2-en-1-amine

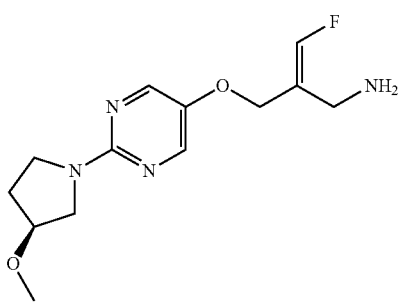 [SMILES: CO[C@H]1CCN(c2ncc(OC/C(=C/F)CN)cn2)C1]

Stir a solution of tert-butyl N-[(E)-3-fluoro-2-[[2-[(3S)-3-methoxypyrrolidin-1-yl]pyrimidin-5-yl]oxymethyl]allyl]carbamate (481 mg, 1.26 mmol) and trifluoroacetic acid (1 mL, 13.23 mmol) in DCM (3 mL) at room temperature for 1 hour. Concentrate the mixture under vacuum. Subject the residue to prep-HPLC: LC Column: XBridge® C18 30×150 mm 5 µm; eluting with 5% 10 mM aqueous $NH_4HCO_3$ in ACN from 0-2 minutes, then a gradient of 6-11% 10 mM aqueous $NH_4HCO_3$ in ACN from 2-12 minutes; stop at 18 minutes; column temp: room temperature; flow rate: 35 mL/minutes, $R_t$=10.6 minutes; monitor by UV to give the title compound (226 mg, 61.7%) as a white solid with an E:Z ratio greater than 20:1. ES/MS (m/z): 283.1 (M+H), $^1$H NMR (500 MHz, $CDCl_3$) δ 1.12-1.78 (br, 2H), 2.07-2.16 (m, 2H), 3.37 (s, 3H), 3.53-3.68 (m, 6H), 4.07 (m, 1H), 4.44 (s, 2H), 6.57 (d, J=83.0 Hz, 1H), 8.12 (s, 2H).

EXAMPLE 6

(3S)-1-[5-[(E)-2-(Aminomethyl)-3-fluoro-allyloxy]pyrimidin-2-yl]pyrrolidin-3-ol; Dihydrochloride

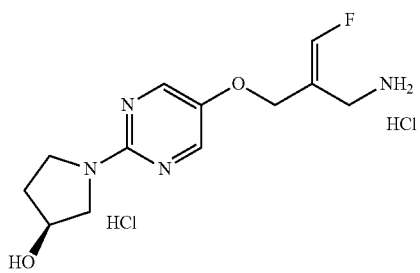 [SMILES: NC/C(=C\F)COc1cnc(N2CC[C@H](O)C2)nc1 ; Cl ; Cl]

Dissolve tert-butyl N-[(E)-3-fluoro-2-[[2-[(3S)-3-hydroxypyrrolidin-1-yl]pyrimidin-5-yl]oxymethyl]allyl]carbamate (605.9 mg, 1.65 mmol) into a mixture of HCl in MeOH (30 mL, 15 mmol, 0.5 mol/L) and HCl in water (5 mL, 60 mmol, 12 mol/L). Stir the resulting clear solution overnight. Concentrate the reaction mixture under vacuum to provide a residue. Subject the residue to pre-HPLC: LC Column: XBridge® C18 30×150 mm 5 µm; $H_2O$ 10 nM $N_4HCO_3$; at room temperature; eluting with 2% ACN for 0-2 minutes, then a gradient of 2-10% ACN for 2-10 minutes, at a flow rate: 35 mL/minutes, $R_t$=8.0 minutes (monitored via UV detection); stopping at 16 mins. Collect the appropriate fractions and concentrate to provide the free base of the title compound. Dissolve the free base compound in 0.5 M HCl in MeOH (15 mL). Concentrate the solution, add water, and then lyophilize to give the title product as a light yellow solid with an E:Z ratio greater than 20:1 (352.7 mg, 0.982 mmol, 59%). ES/MS (m/z): 269 (M+H), $^1$H NMR (500 MHz, $d_6$-DMSO) δ 1.87-1.94 (m, 1H), 1.98-2.05 (m, 1H), 3.44 (d, J=11.5 Hz 1H), 3.51-3.61 (m, 5H), 4.39-4.42 (m, 1H), 4.66 (d, J=3.0 Hz, 2H), 5.33-5.90 (br, 2H), 7.28 (d, J=82.0 Hz, 1H), 8.35 (s, 2H), 8.35-8.44 (br, 3H), $^{19}$F NMR (500 MHz, $d_6$-DMSO) δ 121.9 (s).

Alternate Preparation of Example 6

Dissolve tert-butyl N-[(E)-3-fluoro-2-[[2-[(3S)-3-hydroxypyrrolidin-1-yl]pyrimidin-5-yl]oxymethyl] allyl] carbamate (1.1601 g, 3.15 mmol) in a solution of HCl in EtOAc (50 mL, 50 mmol, 1.0 mol/L) (pre-mixed with 0.5 mol/L HCl in MeOH, 5 mL). Stir the resulting solution overnight. Concentrate the white suspension under vacuum to provide a white powder. Dissolve the white powder in water and lyophilize the solution to provide the title compounds as a light yellow solid (860.7 mg, 2.42 mmol, 77%).

The material prepared as Example 6 is dissolved in water (5 mL) and combined with the material of Alternate Example 6 in water (5 mL). Lyophilize the mixture to give the title compound with an E:Z ratio greater than 20:1 (1.151 g 3.27 mmol). ES/MS m/z: 269 (M+H), $^1$H NMR (500 MHz, $d_6$-DMSO) δ 1.87-1.94 (m, 1H), 1.98-2.05 (m, 1H), 3.44 (d, J=11.5 Hz 1H), 3.51-3.61 (m, 5H), 4.39-4.42 (m, 1H), 4.66 (d, J=3.0 Hz, 2H), 5.33-5.90 (br, 2H), 7.28 (d, J=82.0 Hz, 1H), 8.35 (s, 2H), 8.35-8.44 (br, 3H), $^{19}$F NMR (500 MHz, $d_6$-DMSO) δ 121.9 (s).

Biological Assays
SSAO/VAP-1 In Vitro Activity

Amine oxidase activity of recombinant SSAO, MAOa, and MAOb isoforms are measured using the MAO-Glo™ assay kit from Promega (V1402). Test compounds (with DMSO as vehicle, 0.5% v/v for SSAO) and the enzyme are incubated for 10 mins at room temperature before the addition of the luminogenic substrate. The substrate concentration is 10 µM for human recombinant SSAO. The assays are conducted in a pH 7.4 buffer (50 mM HEPES, 120 mM NaCl, 5 mM KCl, 2 mM $CaCl_2$, 1.4 mM $MgCl_2$, 0.001% Tween-20) in a well-plate. Oxidation of the substrate is conducted for 2 hrs before the addition of detecting reagent according the manufacture's protocol. The $IC_{50}$ value of the tested compounds is calculated by fitting the dose response curve using a 4-parameter non-linear regression routine. The $IC_{50}$ values for the compounds of Example 3, 5, and 6 are listed in Table 2.

TABLE 2

| Ex | hSSAO Inhib Rel $IC_{50}$ (nM) |
| --- | --- |
| 3 | 12 ± 1, n = 5 |
| 5 | 32 ± 7, n = 4 |
| 6 | 52 ± 5, n = 7 |

Data are presented as mean±SEM (SEM=standard error of the mean) for the number of assays (n).

The compounds of the Examples exhibited an $IC_{50}$ for hSSAO of less than 60 nM. The compounds of the Examples exhibited an $IC_{50}$ hMAOa and hMAOb more than 50 µM and 200 µM, respectively, indicating that the compounds of the Examples are selective for hSSAO over either hMAOa or hMAOb.

SSAO Target Engagement

The SSAO activity in rat plasma and liver tissues are measured using the MAO-Glo™ assay kit from Promega (V1402). The residual SSAO activity in rats after compound treatment is estimated by measuring the total amine oxidase activity in plasma or liver lysates that are insensitive to the presence of the MAO inhibitor Clogyline and Pargyline. Rats are administered the compound of Example 2 at the doses of 15, 3, 0.6, 0.12, 0.025, 0.005 mg/kg. The control group is administered with the same volume (2 ml/kg) of the dosing vehicle (hydroxyethyl cellulose 1% w/v, 0.25% Tween 80). Plasma and liver at 2 or 24 hours post compound treatment are harvested and stored at −78° C. until analysis. Tissue lysates are prepared by homogenization in a lysis buffer (20 mM HEPES, pH 7.4, 150 mM NaCl, 1 mM EDTA, 1 mM EGTA, 1% Triton X-100 and 1× Roche Complete protease inhibitor tablet). Tissue particles are removed by centrifugation at 12,000 rpm at 4° C. for 30 minutes. 40 µl of plasma or liver lysates is incubated with Clogyline (10 µM) and Pargyline (10 µM) for 20 minutes at room temperature before the addition of the luminogenic substrate (50 µM) for 60 minutes. The product generated is quantified according to the manufacture's procedure. The fraction of activity that is insensitive to the presence of the MAO inhibitors is used as the surrogate for the residual SSAO activity. The compound of Example 2 was evaluated in the protocol essentially as described above administered at various doses. The results are listed in Table 3.

TABLE 3

SSAO Target Engagement for Example 2

| Dose | SSAO Activity (%) | | |
|---|---|---|---|
| | Plasma | | Liver |
| (mg/kg) | 2 hour | 24 hour | 24 hour |
| Vehicle | 100 ± 7 | 100 ± 9 | 100 ± 11 |
| 0.005 | 31 ± 3 | 70 ± 7 | 75 ± 18 |
| 0.025 | 21 ± 1 | 55 ± 9 | 68 ± 14 |
| 0.12 | 7 ± 1 | 35 ± 4 | 45 ± 8 |
| 0.6 | 4.3 ± 0.8 | 16.3 ± 2.6 | 16.2 ± 2.9 |
| 3 | 3.6 ± 1.0 | 8.8 ± 1.3 | 7.1 ± 1.7 |
| 15 | −0.6 ± 0.3 | 6.6 ± 1.8 | 9.6 ± 2.6 |

Data are presented as mean±SEM, n=6

The results indicate that the compound of Example 2 dose-dependently inhibits SSAO activity in both rat plasma and liver.

Mouse Model of NASH and Fibrosis Induced by 3H Diet

Male C57BL/6N mice are fed with D09100301 diet (Research Diets, 40% fat, 2% cholesterol, 24% fructose, (the, high fat, high cholesterol and high fructose, the "3H diet") for 150 days. Each mouse is then singly housed after 5 days for an acclimation period. Plasma alanine aminotransferase (ALT) and cytokeratin 18 (CK18) are measured. After one week of recovery, the mice are randomized into 5 groups based on their ALT values, CK18 values, and body weight. Animals of each group are administered either vehicle (0.5% methylcellulose (MC)+0.25% Tween 80 in distilled water) or the compound of Example 6 (at a 0.06, 2, 6, and 20 mg/kg dose) once daily in a volume of 5 ml/kg for 11 weeks.

Blood is collected from mice treated with the compound of Example 6 for 76 days 2 hours after the last dose. Compound levels in the plasma are analyzed by mass spectroscopy. The results are listed below in Table 4. Treated mice exhibit a dose-dependent increase in plasma compound levels. All groups of mice treated with Example 6 exhibit a significant decrease in ALT, indicating decreased hepatic lesions in those animals. Animals treated with 6 and 20 mg/kg of the compound of Example 6 also exhibit decreased triglyceride levels in blood.

At the completion of the study, the animals are sacrificed and their livers excised. Two sections of the left and right lobes are fixed in neutral buffered 10% formalin. Liver tissue slides are stained with hematoxylin and eosin (H&E), Sirius red, and Masson's Trichrome to prepare slides for pathological analysis. All specimens are examined microscopically and scored as a modified Brunt score NASH Activity Score. Scores are based on the grading scheme and endpoints as described in Brunt E. M, et al., "Histopathology of nonalcoholic fatty liver disease," World J. of Gastroenterol, 2010, 16(42), 5286-5296. Group means are then calculated for each individual end-point. The following endpoints are used to characterize the fast food model of NASH in mice as modified from NASH endpoints (See Brunt, E. M. "Histopathology of nonalcoholic fatty liver disease," Clin Liver Dis., 2009, 13, 533-544 and Brunt, E. M, et al., "Nonalcoholic steatohepatitis: A proposal for grading and staging the histological lesions", Am J Gastroenterology, 1999, 94(9), 2467-2474.

Histopathological analysis of the livers from the mice treated with the compound of Example 6 is provided in Table 4. The results indicate that there is a significant decrease in hepatic inflammation, macrovesicular vaculation, and perisinusoidal fibrosis in the mice that are treated with 20 mg/kg of the compound of Example 6.

TABLE 4

Efficacy Results for the Compound of Example 6

| Dose (mg/kg) | Nos. of Animals | Plasma Compound Level (ng/ml) | ALT (IU/L)[1] | Plasma TG (mg/dL)[1] |
|---|---|---|---|---|
| Vehicle | 12 | — | 713 ± 43 | 69 ± 4 |
| 0.6 | 13 | 66. ± 5 | 530 ± 45* | 55 ± 6 |
| 2 | 13 | 163 ± 21 | 483 ± 44** | 70 ± 11 |
| 6 | 11 | 560 ± 29 | 495 ± 25* | 46 ± 4* |
| 20 | 11 | 2117 ± 219 | 466 ± 37*** | 45 ± 5* |

[1]MIXED model is applied to compare fold changes from baseline adjusted by baseline between compound treatment groups and vehicle group, (See "Generalized, Linear, and Mixed Models," McCulloch, C. E., and Searle, S. R., Eds. John Wiley and Sons, 2000 and "Mixed-Effects Models in S and S-PLUS", Pinheiro J. C., and Bates, D. M., Eds. Springer, 2000.)

Data are presented as mean ± SEM.

*p < 0.05;

**p < 0.01;

***p < 0.001

TABLE 5

Liver Histopathological Analysis for the Compound of Example 6

| Dose (mg/kg) | Score (0-3)[1] | | | | | |
|---|---|---|---|---|---|---|
| | Hepatic inflammation | | Macrovesicular vaculation | | Perisinusoidal fibrosis | |
| | Left | Right | Left | Right | Left | Right |
| Vehicle | 2.8 ± 0.1 | 2.7 ± 0.1 | 2.8 ± 0.1 | 2.8 ± 0.1 | 2.5 ± 0.2 | 2.3 ± 0.1 |
| 0.6 | 2.6 ± 0.1 | 2.5 ± 0.1 | 2.5 ± 0.1 | 2.6 ± 0.1 | 2.4 ± 0.2 | 1.9 ± 0.2 |
| 2 | 2.5 ± 0.1 | 2.6 ± 0.1 | 2.5 ± 0.1 | 2.7 ± 0.1 | 2.5 ± 0.2 | 1.8 ± 0.2 |
| 6 | 2.5 ± 0.2 | 2.6 ± 0.2 | 2.9 ± 0.1 | 2.7 ± 0.1 | 2.6 ± 0.2 | 2.1 ± 0.3 |
| 20 | 2.1 ± 0.1** | 2.1 ± 0.1* | 2.4 ± 0.2 | 2.3 ± 0.1* | 1.9 ± 0.2 | 1.5 ± 0.2* |

[1]Nonparametric test is applied to compare scores between compound treatment groups and vehicle group. Scores for left and right laterals are compared separately.
Data are presented as mean ± SEM.
*$p < 0.05$;
**$p < 0.01$;
*** $p < 0.001$

What is claimed is:

1. A process for preparing a compound of Formula 2:

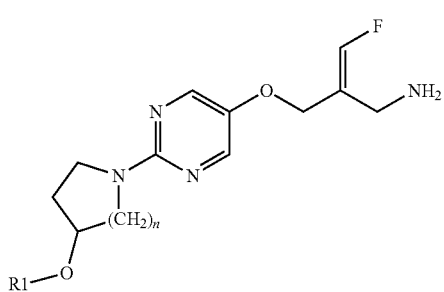

or a pharmaceutically acceptable salt thereof,
wherein:
n is 1 or 2; and
R1 is H or —CH$_3$,
said method comprising the steps of:
a) reacting a compound of the formula

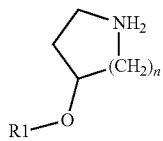

wherein n is 1 or 2; and
R1 is H or —CH$_3$,
with a compound of the formula

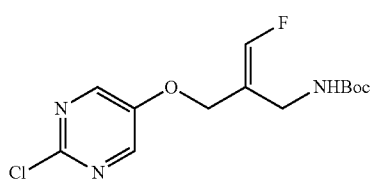 [SMILES: CC(C)(C)OC(=O)NC/C(=C\F)COc1cnc(Cl)nc1]

wherein Boc is tert-butoxycarbonyl,
to form a compound of the formula

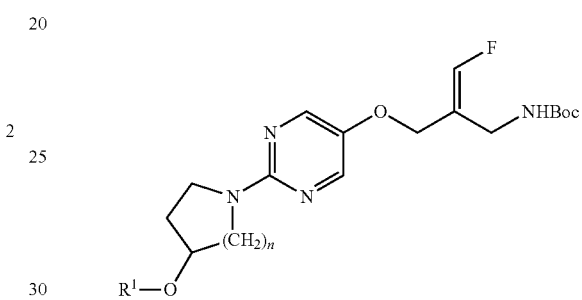

wherein:
n is 1 or 2;
R1 is H or —CH$_3$; and
Boc is tert-butoxycarbonyl; and
b) reacting the compound of the formula

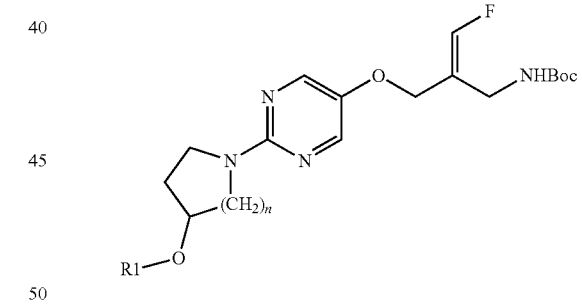

wherein:
n is 1 or 2;
R1 is H or —CH$_3$; and
Boc is tert-butoxycarbonyl,
with an acid to form the compound of Formula 2 or a pharmaceutically acceptable salt thereof.

2. The process of claim 1, wherein the process further comprises reacting the pharmaceutically acceptable salt of the compound of Formula 2 with a base to form the compound of Formula 2.

3. The process of claim 2, further comprising reacting the compound of Formula 2 with an acid to form a different pharmaceutically acceptable salt of the compound of Formula 2.

4. The process of claim 1, wherein n is 1.

5. The process of claim 1, wherein n is 2.

6. The process of claim 1, wherein R1 is H.

7. The process of claim 1, wherein R1 is —CH₃.

8. The process of claim 1, wherein step a) is carried out in the presence of a base.

9. The process of claim 8, wherein the base is N,N-diisopropylethylamine or potassium carbonate.

10. The process of claim 1, wherein step a) uses 1,4-dioxane as solvent.

11. The process of claim 1, wherein the acid in step b) is hydrochloric acid or trifluoroacetic acid.

12. The process of claim 1, wherein the compound of the formula

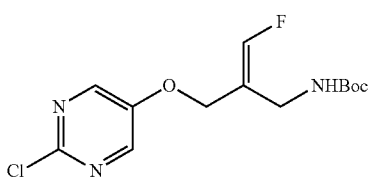 [SMILES: CC(C)(C)OC(=O)NC/C(=C\F)COc1cnc(Cl)nc1]

of step a) is prepared by reacting tert-butyl N-[(E)-2-(bromomethyl)-3-fluoro-allyl]carbamate with 2-chloropyrimidin-5-ol.

13. The process of claim 12, wherein the reaction is carried out in the presence of potassium carbonate.

14. The process of claim 12, wherein the reaction uses dimethylformamide as solvent.

15. The process of claim 1, wherein the compound of Formula 2, or a pharmaceutically acceptable salt thereof, is:

(E)-3-fluoro-2-[[2-(4-methoxy-1-piperidyl)pyrimidin-5-yl]oxymethyl]prop-2-en-1-amine dihydrochloride.

16. The process of claim 1, wherein the compound of Formula 2, or a pharmaceutically acceptable salt thereof, is:

(2E)-3-fluoro-2-({[2-(4-methoxypiperidin-1-yl)pyrimidin-5-yl]oxy}methyl)prop-2-en-1-amine 4-methylbenzenesulfonate.

* * * * *

UNITED STATES PATENT AND TRADEMARK OFFICE
CERTIFICATE OF CORRECTION

PATENT NO. : 10,464,928 B2
APPLICATION NO. : 16/356882
DATED : November 5, 2019
INVENTOR(S) : David Andrew Coates et al.

Page 1 of 1

It is certified that error appears in the above-identified patent and that said Letters Patent is hereby corrected as shown below:

In the Claims

In Claim 1, Column 20, Lines 20-30, delete:

"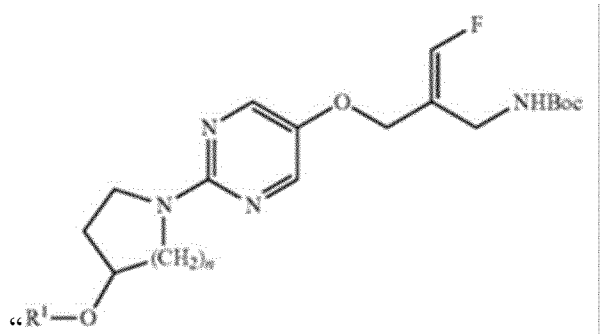"

And insert:

--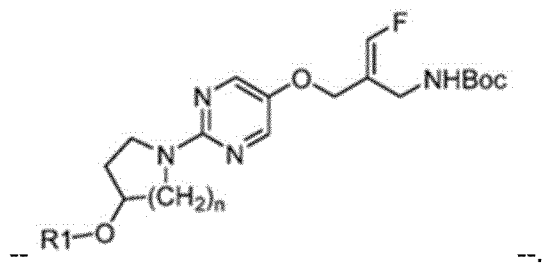--.

Signed and Sealed this
Twenty-eighth Day of January, 2020

Andrei Iancu
*Director of the United States Patent and Trademark Office*